United States Patent [19]

Trenzeluk

[11] Patent Number: 5,279,828

[45] Date of Patent: Jan. 18, 1994

[54] INGESTIBLE MIXTURE CONTAINING CHUCHUHUASHA EXTRACT

[75] Inventor: Theodore Trenzeluk, Manville, N.J.

[73] Assignee: Tecma Laboratories, Inc., Bridgewater, N.J.

[21] Appl. No.: 21,564

[22] Filed: Feb. 24, 1993

Related U.S. Application Data

[63] Continuation-in-part of Ser. No. 697,447, May 9, 1991, abandoned.

[51] Int. Cl.$^5$ .............................................. A61K 35/78
[52] U.S. Cl. .................................. 424/195.1; 514/849; 514/855
[58] Field of Search ..................... 424/195.1; 514/849, 514/855

[56] References Cited

PUBLICATIONS

S. Reis et al., "New Plant Sources for Drugs and Foods from The New York Botanical Garden Herbarius", Harvard Am. Press 1982, p. 167.
CA 96 (21):177916m, Gonzalez, et al., 1982.
CA 85(7):43691y, Martin, et al., 1976.

*Primary Examiner*—John W. Rollins
*Attorney, Agent, or Firm*—R. Martin Oliveras

[57] ABSTRACT

An ingestible mixture containing the extract from the chuchuhuasha plant is useful for the alleviation of cramps, colds, and nasal congestion. The mixture comprises: the therapeutic component being the extract from the chuchuhuasha plant; a taste and fermentation component being honey; and a liquid extraction component being chosen from the group consisting of alcohol and water. According to the present invention, the mixture comprises about 20% to 50% by weight of the extract from the chuchuhuasha plant as the therapeutic component; about 20% to 50% by weight of water or alcohol as the liquid extraction component; and about 25% to 35% by weight of honey as the taste and fermentation component. According to a specific embodiment of the present invention, the mixture comprises about 35% by weight of the extract from the chuchuhuasha plant; about 35% by weigh of water or alcohol; and about 30% by weight of honey. The chuchuhuasha plant is also known by its scientific name Cheiloclinium cognatum as shown on page 167 of the reference "New Plant Sources for Drugs and Foods from the New York Botanical Garden Herbarium" published by the Harvard University Press in 1982.

2 Claims, No Drawings

INGESTIBLE MIXTURE CONTAINING CHUCHUHUASHA EXTRACT

OTHER RELATED APPLICATIONS

This is a continuation-in-part application of prior application Ser. No. 07/697,447, filed May 9, 1991, now abandoned, entitled "Ingestible Mixture Containing Chucchuhuazo Extract" by the same applicant herein.

FIELD OF THE INVENTION

This invention relates to ingestible mixtures and in particular to such a mixture which includes the extract of the chuchuhuasha plant as the therapeutic component.

DISCUSSION OF THE PRIOR ART

Several prior art patents disclose therapeutic mixtures as follows:

a. Field U.S. Pat. No. 112,329 discloses as solution comprising water, potassium nitrate, potassium chlorate, licorice extract, boneset leaves, hemp leaves, stromonium leaves, cabela leaves, Virginia snake root, and gum myrrh;

b. Watts U.S. Pat. No. 230,365 discloses a liniment comprising wild cherry, wild thistle, spearmint, coal oil, turpentine, peppermint, bicarbonate of soda, ammonia, and camphor;

c. Marshall U.S. Pat. No. 915,781 discloses a hair tonic comprising of a intimate mixture of olive oil in an aqueous extract of the leaves of elder, crab apple, morning glory, night shade, wild sage, horseradish, boneset, and sheep sorrel;

d. Chapman U.S. Pat. No. 1,519,755 discloses a poultice preparation comprising a mixture of dried powdered vegetable materials including boneset, sweet fern, and a glutinous material;

e. Fuller U.S. Pat. No. 1,627,963 discloses a fluid extract and tincture comprising a vegetable drug used as a remedial agent and a halogen containing ester of glycerine;

f. Meccas U.S. Pat. No. 2,370,561 discloses a therapeutic product comprising the active molecular structure of allantoin and a sulfa compound;

g. Mahon U.S. Pat. No. 2,843,522 discloses a water repellant perianal ointment comprising petrolatum, para-di-isobutyl-cresoxy-ethyl-di-methyl-benzyl ammonium chloride, and calcium caseinate;

h. Maret U.S. Pat. No. 3,878,197 discloses the process comprising the steps of cutting the rind and aloins of the aloe vera leaf from the gel, and agitating the gel under ultraviolet radiation in a digestion liquid containing amine, phosphorous ions, and potassium ions at a given pH;

i. Cobble U.S. Pat. No. 3,892,853 discloses the process comprising the steps of mechanical separation, homogenization, addition of hydrogen peroxide, heating to a given temperature, addition of an effective preparation of a non-toxic buffer to maintain a given pH range;

j. Seegall U.S. Pat. No. 3,920,816 discloses a composition consisting of the juice from the freshly cut leaves of the plant aloe arboescens obtained by extracting the leaves in boiling bee honey;

k. Coats U.S. Pat. No. 4,178,372 discloses a process comprising the steps of mechanical separation, extrusion, heating to a given temperature range, addition of a catalytic amount of hydrogen peroxide, addition of ascorbic acid, and addition of citric acid to maintain a given pH range;

l. Takahashi U.S. Pat. No. 4,215,049 discloses a hiyodorolacton-B having a given formula;

m. Spies U.S. Pat. No. 4,258,035 discloses a mixture of herbel components consisting of camfrey, mullein, fenugeek, nettle, broom tops, and boneset;

n. De Navarre U.S. Pat. No. 4,302,443 discloses a composition comprising aluminum chlorhydroxide and an extract of the aloe vera plant;

o. Mihalovits U.S. Pat. No. 4,369,180 discloses a preparation comprising aloe vera, citric acid, potassium sorbate, sodium benzoate, cornstarch, albumin, hydroxy-propyl-methyl cellulose, allantoin, vitamin A, vitamin D2, and vitamin E;

p. Maughan U.S. Pat. No. 4,446,131 discloses a process comprising the steps of heating to a given temperature range, addition of ascorbic acid, maintaining the mixture within a given temperature range, and cooling to ambient temperature in less than one hour;

q. Halsam et al U.S. Pat. No. 4,44,751 discloses an aqueous composition comprising a given polymer, a pharmaceutic or diagnostic agent, and a n pharmaceutically acceptable acid to base to adjust the pH within a certain range;

r. Millard U.S. Pat. No. 4,505,902 discloses a preparation comprising mineral oil, apricot kernal oil, avocado oil, cod liver oil, propylparaben, and butyl-hydroxyanisole.

The above cited prior art patents do not disclose the present ingestible mixture containing the extract of chuchuhuasha as the therapeutic component.

SUMMARY OF THE PRESENT INVENTION

According to the present invention:

a. an ingestible mixture contains the extract from the chuchuhuasha plant and is useful for the alleviation of cramps, colds, and nasal congestion;

b. the mixture comprises: a therapeutic component being the extract from the chuchuhuasha plant; a taste and fermentation component being honey; and a liquid extraction component being alcohol or water;

c. the mixture comprises about 20% to 50% by weight of the extract from the chuchuhuasha plant as the therapeutic component; about 20% to 50% by weight of water or alcohol as the liquid extraction component; and about 25% to 35% by weight of honey as the taste and fermentation component;

d. according to a specific embodiment, the mixture comprises about 35% by weight of the extract from the chuchuhuasha plant; about 35% by weight of water or alcohol; and about 30% by weight of honey;

e. the above components are mixed together from 2 days to 5 days; then the mixture is heated up to about 70 degrees centigrade for about ½ hour to about 1 hour; then the mixture is blended together for about 2 hours; and then the mixture is filtered to remove any remaining particles.

DETAILED DESCRIPTION

An ingestible mixture contains the extract from the chuchuhuasha plant and is useful for the alleviation of cramps, colds, and nasal congestion. The mixture comprises: a therapeutic component being the extract from the chuchuhasha plant; a taste and fermentation component being honey; and a liquid extraction component being alcohol or water. The mixture comprises about 20% to 50% by weight of the extract from the chuchuhuasha plant as the therapeutic component; about 20% to 50% by weight of water or alcohol as the liquid extraction component; and about 25% to 35% by weight of honey as the taste and fermentation component. According to a specific embodiment of the present invention, the mixture comprises about 35% by weight of the extract from the chuchuhuasha plant; about 35% by weight of water or alcohol; and about 30% by weight of honey. The above components are mixed together from 2 days to 5 days; then the mixture is heated up to about 70 degrees centigrade for about ½ hour to about 1 hour; then the mixture is blended together for about 2 hours; and then the mixture is filtered to remove any remaining particles.

EXAMPLE 1

A teenage female with menstrual cramps ingested between 1 teaspoon and 1 tablespoon of the mixture and experienced relief in 1 day.

EXAMPLE 2

A 20 year old male with a cold and nasal congestion ingested between 1 teaspoon and 1 tablespoon of the mixture and experienced relief in 4 days.

While the arrangement according to the present invention has been described in terms of a specific embodiment, it will be apparent to those skilled in the art that many modifications are possible within the spirit and scope of the disclosed principle.

I claim:
1. An ingestible mixture for the alleviation of cramps, colds, and nasal congestion comprising:
 a. about 20% to 50% by weight of the extract from the chuchuhuasha plant as the therapeutic component;
 b. about 20% to 50% by weight of a liquid extraction component being chosen from the group consisting of water and alcohol; and
 c. about 25% to 35% by weight of honey as the taste and fermentation component;
 wherein said ingestible mixture is made as follows:
 d. mixing said components together from 2 days to 5 days;
 e. heating said mixture up to about 70 degrees centigrade for about ½ hour to about 1 hour;
 f. blending said mixture together for about 2 hours;
 g. filtering said mixture to remove any remaining particles.
2. The ingestible mixture of claim 1 for the alleviation of cramps, colds, and nasal congestion comprising:
 a. about 35% by weight of the extract from the chuchuhuasha plant;
 b. about 35% by weight of said liquid extraction component; and
 c. about 30% by weight of honey.

* * * * *